Figure 1:
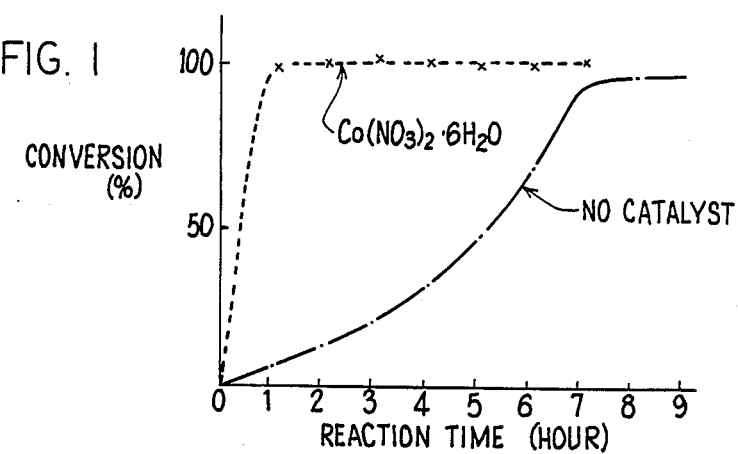

United States Patent [19]

Hinenoya et al.

[11] Patent Number: 4,830,789

[45] Date of Patent: May 16, 1989

[54] PROCESS FOR PRODUCING CARBOXYLIC ACID ANHYDRIDES

[75] Inventors: Masayoshi Hinenoya; Mamoru Endo, both of Arai, Japan

[73] Assignee: Daicel Chemical Industries, Ltd., Sakai, Japan

[21] Appl. No.: 946,462

[22] Filed: Dec. 24, 1986

[30] Foreign Application Priority Data

Dec. 25, 1985 [JP] Japan ................................ 60-296114
Dec. 25, 1985 [JP] Japan ................................ 60-296115
Apr. 18, 1986 [JP] Japan ................................ 61-89242

[51] Int. Cl.$^4$ ............................................. C07C 53/00
[52] U.S. Cl. ................................... 660/546; 549/247
[58] Field of Search ........................ 260/546; 549/247

[56] References Cited

U.S. PATENT DOCUMENTS 2,163,013 6/1939 Schulz ................................ 260/546
3,045,045 7/1962 Melchiore ........................ 260/546

Primary Examiner—Paul J. Killos
Attorney, Agent, or Firm—Flynn, Thiel, Boutell & Tanis

[57] ABSTRACT

The present invention provides (1) a process for producing a colorless aromatic acid anhydride having a high purity in a high yield by reacting an aromatic carboxylic acid having a carboxyl group bonded to the aromatic nucleus with a lower aliphatic acid anhydride in the presence of at least one metal ion selected from the group consisting of ions of metals of Groups, I, II, III, V, VII and VIII of the periodic table and (2) a process for producing an acid anhydride by an exchange reaction of an organic carboxylic acid anhydride and a carboxylic acid in the presence of at least 5 ppm of at least one metal ion selected from the group consisting of Co, Ni, Mn, Fe, Li, Na, K, Mg, Ca, Cu, Zn, Al, Ti and V ions.

16 Claims, 4 Drawing Sheets

PROCESS FOR PRODUCING CARBOXYLIC ACID ANHYDRIDES

FIELD OF THE INVENTION

The present invention relates to (1) a process for producing an aromatic acid anhydride from an aromatic carboxylic acid and an acid anhydride.

The present invention relates also to (2) a process for producing an acid anhydride by exchange reaction of an organic carboxylic acid anhydride and a carboxylic acid.

STATEMENT OF PRIOR ARTS (1) Aromatic acid anhydrides, particularly pyromellitic anhydride (hereinafter referred to as PMDA) and 3,4,3′, 4′-benzophenonetetracarboxylic acid dianhydride (hereinafter referred to as BTDA), are important industrial starting materials used widely as curing agents for heat-resistant resins such as polyimide or epoxy resins.

The grades of PMDA and BTDA are various and they are selected depending on the use. Recently, not only a high purity but also a low degree of coloring are required of them. The products having a low purity or a high degree of coloring have only a low commercial value.

Known processes for the production of BTDA or PMDA include (1) one wherein a corresponding free acid is heated to a high temperature, (2) one wherein the free acid is heated together with an acid anhydride such as acetic anhydride and (3) one wherein a corresponding alkyl-substituted compound is oxidized in gas phase followed by dehydration. Among them, the processes (1) and (3) require such a high temperature of above 200° C. that the obtained product is colored seriously. Though the product having a relatively low degree of coloring can be obtained by the process (2) wherein an acid anhydride is used, it is difficult usually to obtain a product having a purity of 99 % or higher by this process even when the reaction temperature is elevated, reaction time is prolonged or the amount of the acid anhydride used is increased, and rather the degree of coloring is increased.

(2) Among various known processes for producing carboxylic acid anhydrides, the process wherein an acid anhydride such as acetic anhydride is used is one of the industrially most useful processes, since no special reaction device is necessary. The mechanism of this reaction is supposed to be as shown by the following general formula (1) and the reaction rate is increased usually by heating:

$$R_1COH + (R_2C)_2O \rightleftharpoons R_2COH + R_1C-O-CR_2$$
$$\updownarrow R_1CO_2H$$
$$(R_1C)_2O + R_2COH$$

(with carbonyl oxygens as drawn)

wherein $R_1$ and $R_2$ represent each a substituted or unsubstituted alkyl or aryl group or the like.

The conventional technique wherein the reaction rate is increased by heating to a high temperature of 100° C. or higher has problems, since the starting acid anhydride and the resulting acid anhydride have a relatively low thermal stability. For example, when acetic anhydride is used as the starting material, it is decomposed to form acetic acid and a ketene, which is polymerized to form a tarry substance.

SUMMARY OF THE INVENTION

An object of the present invention is to solve these problems.

Another object of the invention is to obtain an aromatic acid anhydride having a high purity and a low degree of coloring by the above-mentioned process wherein an acid anhydride is used.

BRIEF DESCRIPTION OF THE DRAWINGS (1) FIGS. 1, 2, 3, 4, 5 and 6 are graphs showing the results of Examples 2, 3, 4, 5, 7 and 10, respectively.

Figure 7:
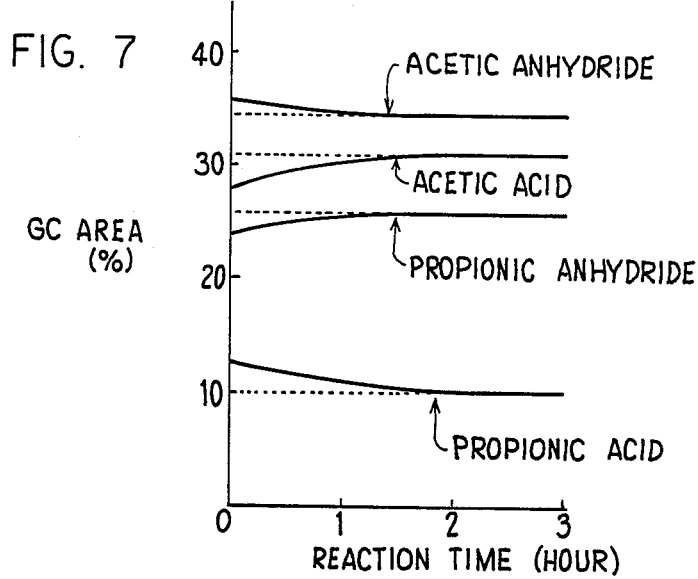
Figure 8:
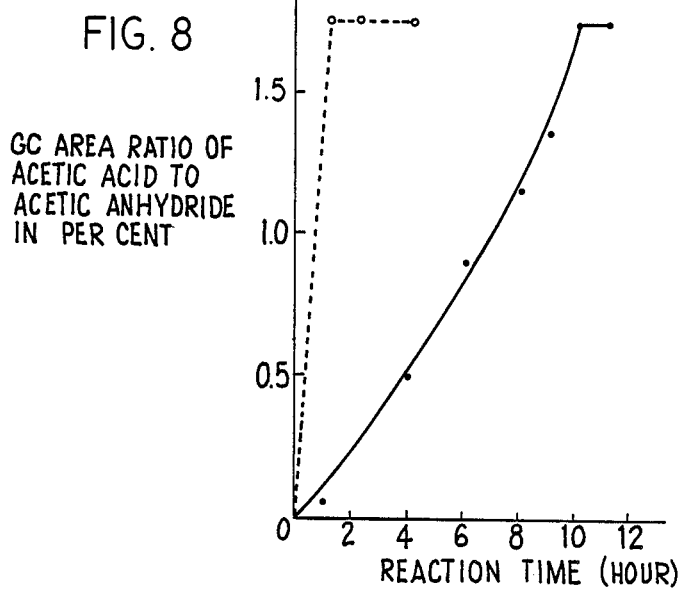

(2) FIGS. 7 and 8 are graphs showing the results of Examples 13 and 14, respectively.

Figure 9:
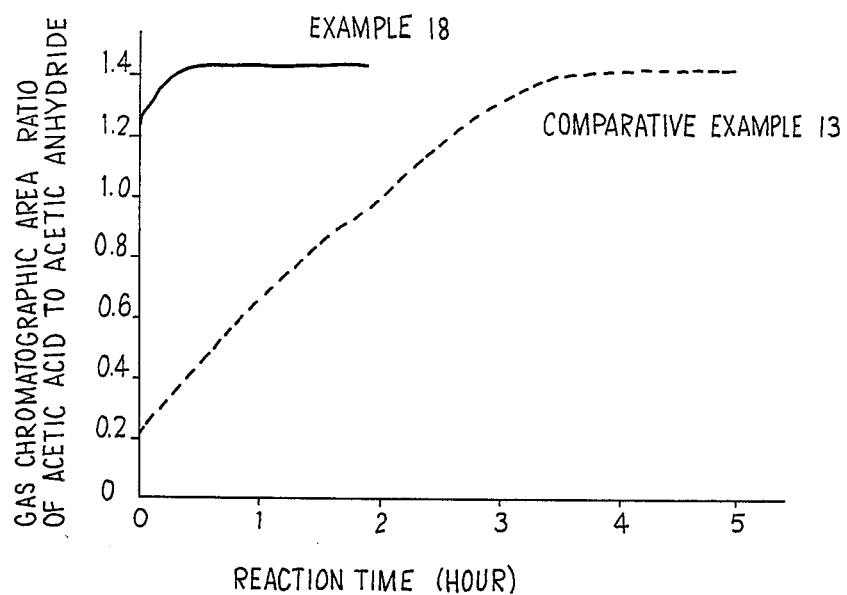
Figure 10:
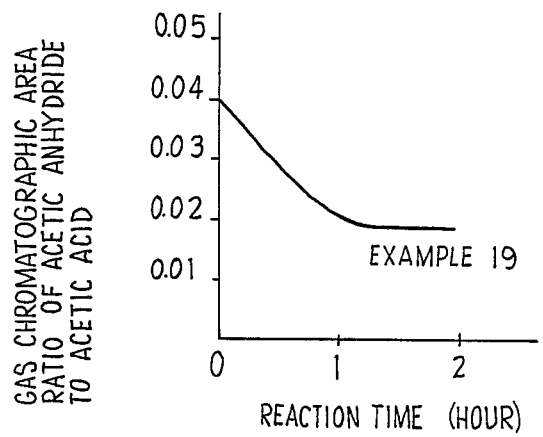

(3) FIGS. 9 and 10 show a reaction rate in examples and a comparative example.

After intensive investigations of processes for the production of BTDA or PMDA, the inventors have found that the product having a high purity and a low degree of coloring can be obtained under mild conditions in a quite short time by carrying out the reaction in the presence of a special metal ion.

An organic carboxylic acid anhydride is produced in the invention by the step of reacting an organic carboxylic acid with a lower aliphatic acid anhydride in the presence of at least one metal ion selected from the group consisting of Ti and metals of Groups I, II, III, V, VII and VIII of the periodic table.

It is preferable that said organic carboxylic acid is an aromatic carboxylic acid having a carboxylic group(s) on the aromatic ring thereof and said metal ion is selected from the group of metals of Groups I, II, III, V, VII and VIII of the periodic table. It is also preferable that said metal ion is an ion selected from the group consisting of Co, Ni, Mn, Fe, Li, Na, K, Mg, Ba, Ca, Cu, Zn, Al, Ti and V and is present in an amount of 5 ppm or more.

It is preferable that said metal ion is present at 5 ppm or more.

The metal ion is used in the form of its salt such as nitrate or acetate or, alternatively, its hydroxide or chloride.

Among the above-mentioned metal ions, Co, Ni, Mn, Fe, Li, Na, K, Mg, Ba, Ca, Cu, Zn, Al and V are preferred. Among them, Co, Ni, Mn and Mg are particularly preferred from the viewpoint of the reaction rate. The concentration of the metal ion in the reaction system is preferably at least 5 ppm.

The lower aliphatic acid anhydrides are preferably those having 1 to 5 carbon atoms, such as acetic and propionic anhydrides. They may be used either alone or in the form of a mixture of them.

The aromatic carboxylic acids having a carboxyl group bonded to the aromatic nucleus are not particularly limited and they include, for example, monocarboxylic, dicarboxylic, tricarboxylic and tetracarboxylic acids. Among them, polycarboxylic acids having the carboxyl groups in o- or para-positions are preferred in the present invention. Examples of them include benzoic, phthalic, trimellitic, pyromellitic, 3,4,3′, 4′-benzophenonetetracarboxylic, 3,3′, 4,4′-diphenyltetracarboxylic, 1,2,5,6-naphthalenetetracarboxylic, 2,3,6,7-naphthalenetetracarboxylic and 2,2′, 3,3′-diphenyltetracarboxylic acids as well as 2,2-bis(3,4-dicarboxyphenyl)-propane, bis(3,4-dicarboxyphenyl) sulfone and bis(3,4-dicarboxyphenyl) ether.

These aromatic carboxylic acids may be halogenated ones having a nucleus substituted with, for example, chlorine.

The reaction of, for example, pyromellitic acid (PMA) with acetic anhydride according to the process of the present invention is shown by the following formula:

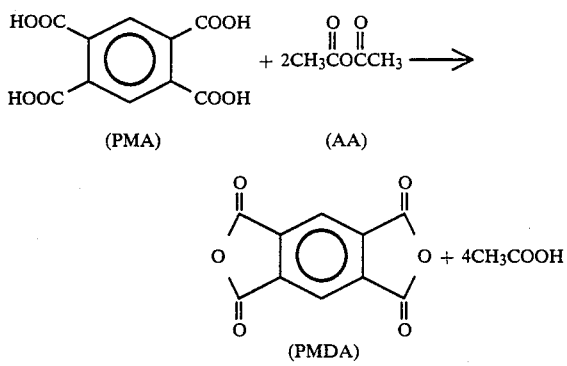

The reaction temperature in the process of the present invention is in the range of preferably 10° C. to around the boiling point of the dehydrating agent (lower aliphatic acid anhydride) and particularly preferably about 50° to 130° C. from the economical viewpoint. point.

The dehydrating agent is used in at least an amount equivalent to the aromatic carboxylic acid used, preferably 1.5 to 2.5 equivalents per equivalent of said acid, since it is used also as the reaction solvent.

According to the process of the present invention, the aromatic acid anhydrides having a high purity and a low degree of coloring can be obtained under mild conditions in a short time.

(2) After further intensive investigations of processes for accelerating the exchange reaction between an organic carboxylic acid anhydride and a carboxylic acid, the inventors have found that the reaction is accelerated remarkably by adding a specified metal ion as the catalyst. The present invention has been completed on the basis of this finding.

The present invention relates to a process for producing an acid anhydride characterized in that the exchange reaction of an organic carboxylic acid anhydride and carboxylic acid is carried out in the presence of at least 5 ppm of at least one metal ion selected from the group consisting of Co, Ni, Mn, Fe, Li, Na, K, Mg, Ca, Cu, Zn, Al, Ti and V ions.

The present invention can be carried out easily by merely adding a catalytic amount of a salt or hydroxide of the above-mentioned metal(s) to a mixture of the organic carboxylic acid anhydride and the carboxylic acid.

According to the present invention, the metal ion is used in the form of its salt such as nitrate or acetate or, alternatively, its hydroxide or chloride. Among the above-mentioned metal ions, Co, Ni and Mn are particularly preferred from the viewpoint of the reaction rate.

The metal ions must be contained in an amount of at least 5 ppm in the reaction system to exhibit their catalytic effects.

The organic carboxylic acid anhydrides are fatty acid anhydrides having 1 to 5 carbon atoms, such as acetic and propionic anhydrides. They may be used also in the form of their mixture.

The carboxylic acids of the present invention are not particularly limited and any of those which can be converted into the corresponding anhydrides by the exchange reaction with the acid anhydride may be used. They include aliphatic, aromatic, alicyclic and heterocyclic mono-, di-, tri-, tetra- and other polycarboxylic acids. Among them, aliphatic carboxylic acids are preferred.

Examples of the carboxylic acids include propionic, succinic, maleic, phenylpropionic, monochloroacetic and acrylic acids.

The reaction temperature in the process of the present invention is selected suitably depending on the starting materials used. Usually, the temperature is preferably in the range of about 10° C. to around the boiling point of the starting material or the product.

The organic carboxylic acid anhydride is used in an amount of at least 1 equivalent per equivalent of the carboxylic acid in the present invention. In the reaction according to the present invention, the conversion is determined by the thermodynamic stabilities of the respective components at the reaction temperature, since it is an equilibrium reaction. When it is desired to use the anhydride in an as small as possible amount, the formed acid (such as acetic acid formed when acetic anhydride is used) is removed from the reaction system by distillation or the like. In this case, a substantially stoichiometric amount of acetic anhydride will suffice. Also when the intended anhydride is removed from the reaction system in the form of crystals, the object of the invention can be attained with a substantially stoichiometric amount of acetic anhydride.

When the catalyst of the present invention is used, the reaction is completed in a short period of time under mild conditions and the formation of a tarry substance is inhibited.

Further, the production of a thermally unstable substance is made possible according to the present invention.

[EXAMPLES]

In the following examples and comparative examples, the degree of coloring (APHA) was determined after dissolving 5 g of the sample in 50 ml of acetone.

COMPARATIVE EXAMPLES 1

90 g of pyromellitic acid (PMA) having a purity of 98% and 152 g of acetic anhydride (AA) (molar ratio of AA/PMA=4.26) were placed in a flask and the pot temperature was elevated to 130° C. under stirring in 1 h. The temperature was maintained at 130° C. for 5 h and then lowered to 25° C. in 1 h.

The reaction liquor was filtered to obtain wet crystals, which were dried in vacuum to obtain 69.2 g of white PMDA. The product has a purity of 98.3% and APHA of 35. The yield was 89.6%.

COMPARATIVE EXAMPLES 2 and 3

The same procedure as in Comparative Example 1 was repeated except that the amount of feed AA and reaction time were altered. The results are shown in Table 1 together with those of Comparative Example 1.

TABLE 1

|  | AA/PMA (molar ratio) | Reaction time (h) | Purity of PMDA (%) | APHA |
| --- | --- | --- | --- | --- |
| Comp. Ex. 1 | 4.26 | 5 | 98.3 | 35 |
| Comp. Ex. 2 | 4.32 | 7 | 98.5 | 45 |
| Comp. Ex. 3 | 5.08 | 5 | 98.0 | 45 |

It is apparent from Table 1 that in the absence of the metal ion, the purity of PMDA could not be increased even when the amount of feed AA was increased or the reaction time was prolonged.

EXAMPLE 1

The reaction was carried out in the same manner as in Comparative Example 1 except that 0.1 g of cobalt nitrate [$Co(NO_3)_2 \cdot 6H_2O$] was added as the catalyst (Co/PMA=225 ppm). 69.3 g of white PMDA was obtained. The product had a purity of 99.5 % and APHA of 35. The yield was 89.6%.

EXAMPLE 2 AND COMPARATIVE EXAMPLE 4

90 g of PMA having a purity of 98% and 152 g of acetic anhydride were placed in a flask and the pot temperature was elevated to 70° C. under stirring in 1 h. Thereafter, the reaction was carried out at a temperature of 70° C. In the course of the reaction, the reaction liquor was sampled at given time intervals and subjected to GC analysis to determine the conversion of PMA into PMDA. The same procedure as above was repeated except that 0.1 g of cobalt nitrate was added as the catalyst and the relationship between the reaction time and conversion was examined at a pot temperature of 70° C. The results are shown in FIG. 1. PMDA obtained in Example 2 had a purity of 99.3% and APHA of 25.

It is apparent from FIG. 1 that when the catalyst was used, the reaction was completed in a short period of time even at a low temperature and, therefore, the colorless product having a quite high quality could be obtained.

EXAMPLE 3 AND COMPARATIVE EXAMPLE 5

Figure 2:
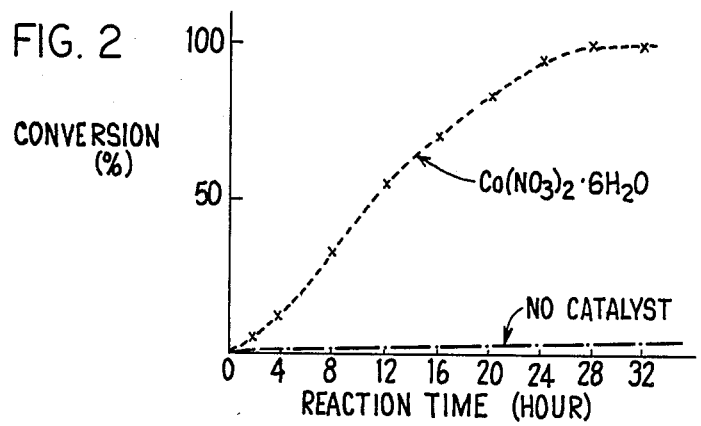

The same procedure as in Example 2 and Comparative Example 4 was repeated except that the temperature was altered to 20° C. The results are shown in FIG. 2.

EXAMPLE 4

Figure 3:
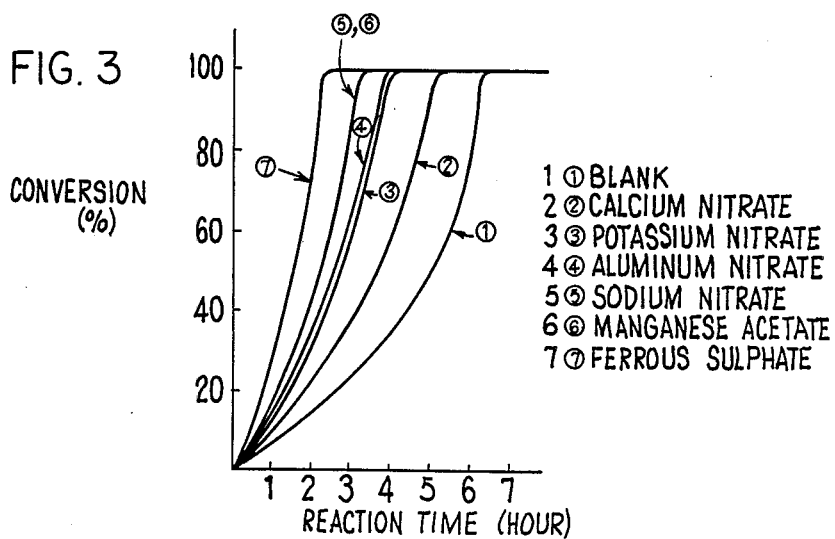
Figure 4:
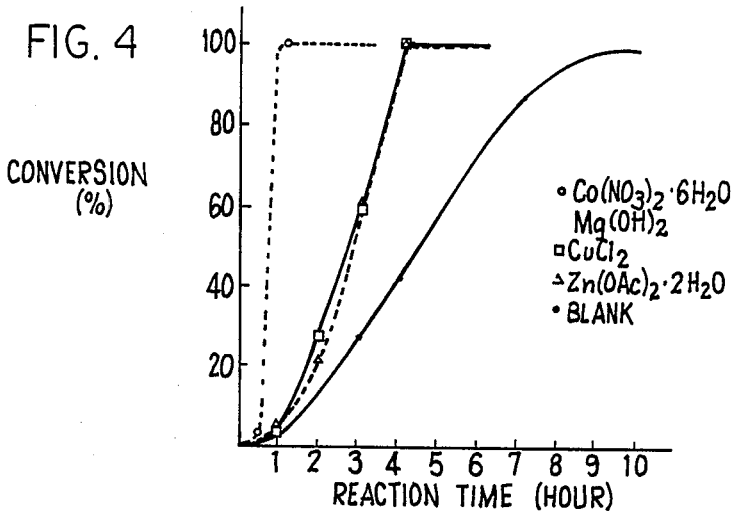
Figure 5:
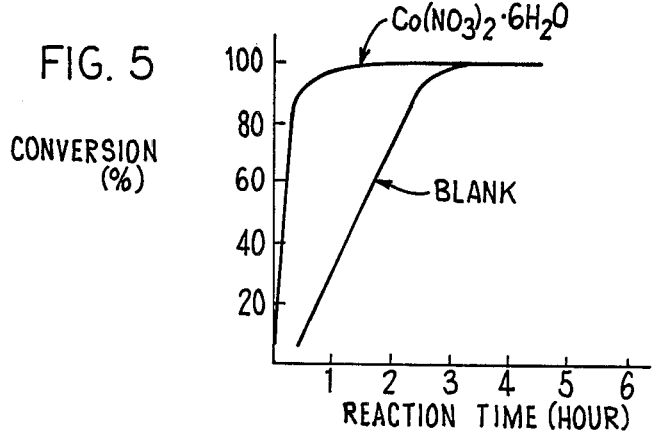

The same procedure as in Example 2 was repeated except that 100 mg of cobalt acetate [$Co(CH_3CO_2)_2 \cdot 4H_2O$], 110 mg of ferrous sulfate ($FeSO_4 \cdot 7H_2O$), 100 mg of calcium nitrate [$Ca(NO_3)_2 \cdot 4H_2O$], 47 mg of potassium nitrate, 110 mg of nickel nitrate [$Ni(NO_3)_2 \cdot 6H_2O$], 100 mg of manganese acetate [$Mn(CH_3CO_2)_2 \cdot 4H_2O$], 100 mg of sodium nitrate or 350 mg of aluminum nitrate [$Al(NO_3)_3 \cdot 9H_2O$] was added as the catalyst. The relationship between the reaction time and conversion in each case is shown in FIG. 3. When cobalt acetate or nickel nitrate was used, the reaction was completed before the temperature elevation was completed.

EXAMPLE 5

150 g of 3,4,3',4'-benzophenonetetracarboxylic acid (BTCA) having a purity of 99.5% and 184 g of acetic anhydride were placed in a flask. 100 mg of cobalt nitrate, 36 mg of magnesium hydroxide, 128 mg of zinc acetate or 23 mg of cuprous chloride was added thereto as the catalyst. The temperature was elevated to 70° C. in 1 h and then the conversion was traced at 70° C. according to gas chromatography to obtain the results shown in FIG. 4.

When no catalyst was used, 9 to 10 h was required to complete the reaction. When cobalt or magnesium was used, the reaction was completed before the temperature elevation was completed. When copper or zinc was used, the reaction was completed in 4 h.

EXAMPLE 6 AND COMPARATIVE EXAMPLE 7

150 g of BTCA having a purity of 99.5% and 184 g of acetic anhydride were placed in a flask. Cobalt nitrate catalyst was added thereto in Example 6 or none was added in Comparative Example 7. The mixture was heated to a reaction temperature of 105° C. for 4 h and then cooled to 25° C. The reaction liquor was filtered to obtain wet crystals, which were dried in vacuum to obtain BTDA. The results are shown in Table 2.

TABLE 2

|  | Catalyst | Co/BTCA (ppm) | Yield | Purity |
| --- | --- | --- | --- | --- |
| Ex. 6 | $Co(NO_3)_2 \cdot 6H_2O$ addition | 135 | 91.0% | 99.3% |
| Comp. Ex. 7 | none | 0 | 91.0% | 98.5% |

COMPARATIVE EXAMPLE 8

The reaction was carried out in the same manner as in Example 2 except that 0.11 g of chromium acetate was used as the catalyst. 7 to 8 h was required for completion of the reaction and no catalytic effect was recognized.

COMPARATIVE EXAMPLE 9

The reaction was carried out in the same manner as in Example 2 except that 37 mg of stannous chloride was used as the catalyst. 6 to 7 h was required for completion of the reaction and no catalytic effect was recognized.

EXAMPLE 7

100 g of BTCA, 157 g of propionic anhydride and 154 mg of cobalt nitrate were placed in a flask and the temperature was elevated to 100° C. in 1 h. Thereafter, the pot temperature was maintained at 100 to 105° C. The conversion was traced to obtain the results shown in FIG. 5.

EXAMPLE 8

The reaction was carried out in the same manner as in Example 2 except that the amount of cobalt nitrate was reduced to 15 mg (Co concentration in the reaction system: 12 ppm). The reaction was completed in 2 h and sufficient catalytic effects were exhibited.

EXAMPLE 9

The reaction was carried out in the same manner as in Example 1 except that a mixture of 0.1 g of cobalt nitrate and 0.1 g of manganese acetate was used as the catalyst. The obtained PMDA had a purity of as high as 99.8%.

EXAMPLE 10 AND COMPARATIVE EXAMPLE 10

90 g of PMA having a purity of 98 % and 152 g of acetic anhydride were placed in a flask and the pot temperature was elevated to 70° C. under stirring in 1 h. Then, the reaction was carried out at that tempeature. In the course of the reaction, the reaction liquor was sampled at given time intervals and subjected to GC analysis to determine the conversion of PMA into PMDA. The same procedure as above was repeated except that 70 mg of barium hydroxide was added as the catalyst and the relationship between the reaction time and conversion was examined while the pot temperature was kept at 70° C. The results are shown in FIG. 6.

Figure 6:
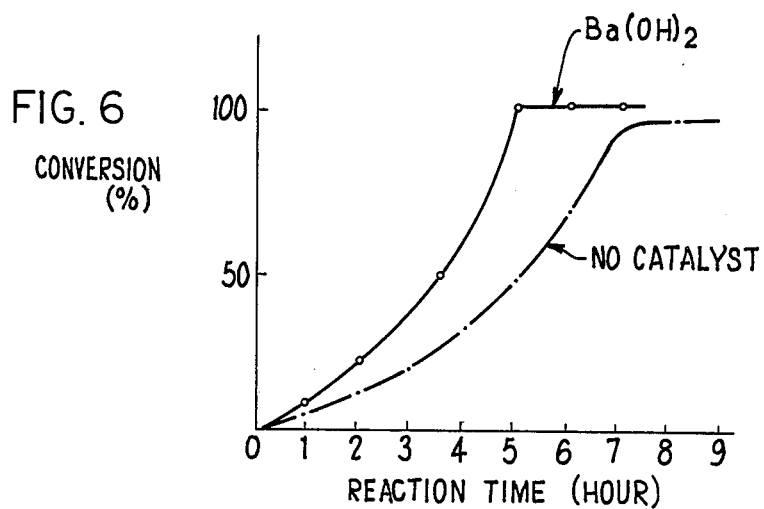

It is apparent from FIG. 6 that when the catalyst was used, the reaction was completed in a short period of time even at a low temperature and, therefore, the colorless product having a quite high quality could be obtained.

EXAMPLE 11

150 g of 3,4,3′, 4′-benzophenonetetracarboxylic acid (BTCA) having a purity of 99.5 % and 184 g of acetic anhydride were placed in a flask. 84 mg of barium hydroxide was added thereto and the temperature was elevated to 70° C. in 1 h. Thereafter, the conversion was traced according to gas chromatography at 70° C. The reaction was completed in 3.5 h.

When no catalyst was used, 9 to 10 h was required for completion of the reaction. Thus, the effects of barium hydroxide were apparent.

EXAMPLE 12

150 g of BTCA having a purity of 99.5% and 180 g of acetic anhydride were placed in a flask. 46 mg of calcium hydroxide was added thereto as the catalyst. The temperature was elevated to 70° C. in 1 h and then the conversion was traced according to gas chromatography at 70° C. The reaction was completed 30 min after the temperature elevation. Apparently, the reaction rate was higher and the effects of the catalyst were more remarkable than those obtained when calcium nitrate was used.

EXAMPLE 13 AND COMPARATIVE EXAMPLE 11

102 g of acetic anhydride and 74 g of propionic acid were placed in a flask and the temperature was elevated to 70° C. in 1 h. The reaction was traced according to gas chromatography while the temperature was maintained at 70° C.

The results are shown in FIG. 7, which indicate that 2 h was required for attaining an equilibrium reaction (see the solid lines in FIG. 7).

When the same procedure as above was repeated except that 0.8 g of cobalt nitrate was used as the catalyst, the reaction reached equilibrium after stirring of 10 min at 20° C. (see broken lines in FIG. 7). No tarry product was formed.

EXAMPLE 14

88.5 g of succinic acid and 153 g of acetic anhydride were placed in a flask and the temperature was elevated to 50° C. in 1 h. The ratio of by-product acetic acid to acetic anhydride was traced according to gas chromatography while the temperature was maintained at 50° C. (see solid line in FIG. 8).

When the reaction was carried out under the same conditions as above except that 0.1 g of cobalt nitrate $[Co(NO_3)_2 \cdot 6H_2O]$ was added, the reaction was completed before completion of the temperature elevation. When the amount of cobalt nitrate was reduced to 20 mg, the similar results were obtained (see broken line in Fig. 8). No tarry product was formed.

EXAMPLES 15 to 18 AND COMPARATIVE EXAMPLE 12

200 g of ethyl acetate, 32.5 g of monochloroacetic acid (MCA) and 25 g of a catalyst listed in Table 3 were introduced into a 500 ml separable flask add the mixture was heated up to a temperatute given in Table 3. At the given temperature, 17.5 g of acetic anhydride (AA) was added to the mixture and the reaction was continued. After the addition of the acetic anhydride, sampling was conducted from the reaction mixture in 5, 30 and 60 minutes. It was analyzed with gas chromatography in view of monochloroacetic acid and acetic anhydride. A reaction rate constant k was calculated with the following equation:

$$\frac{d(MCA)}{dt} = k(MCA)^2 \times (AA)$$

Results are shown in Table 3.

TABLE 3

| | catalyst | amount (ppm) | reaction temp. (°C.) | k ($l^2/mol^2 \cdot hr$) |
|---|---|---|---|---|
| Example 15 | Ni(NO₃)₂·6H₂O | 100 | 40 | 28.4 |
| | ″ | | 60 | 49.7 |
| Example 16 | Co(NO₃)₂·6H₂O | ″ | 40 | 20.0 |
| Example 17 | MgCl₂ | ″ | 40 | 95.9 |
| | | ″ | 60 | 113.1 |
| Example 18 | CaCl₂ | ″ | 40 | 51.0 |
| | | ″ | 60 | 70.8 |
| Comparative Example 12 | no | 0 | 40 | 4.9 |
| | ″ | | 60 | 9.5 |

EXAMPLE 19 AND COMPARATIVE EXAMPLE 13

Fifty grams of itaconic acid and 78.5 g of acetic anhydride were introduced into a flask. Then 0.09 g of magnesium acetate having the formula: Mg(CH3CO2)2.4-H2O for a catalyst was added thereto. The reaction mixture was heated up to 40° C. to proceed with a reaction. The starting of the reaction, that is, zero time, was taken for a point when the reaction temperature reached 40° C. After that, a ratio of the produced acetic acid to acetic anhydride was periodically determined with gas chromatography.

Separately a control test was conducted in the same way as above except that magnesium acetate was not added.

Results are shown in FIG. 9.

It is understood from the results that the reaction for anhydration had been nearly finished during the heating step in the example using the catalyst. It is expected that the example might be effectively worked at a lower temperature. The reaction time of the example was shortened by 1/7 from that of the comparative example using no catalyst.

EXAMPLE 20 AND COMPARATIVE EXAMPLE 14

Fifty grams of itaconic acid and 43.2 g of acetic anhydride, a molar ratio of the former the latter being one, were mixed with 0.09 g of magnesium acetate. The reaction was effected in the same way as in Example 19.

Results are shown in FIG. 10. It is understood that the reaction had finished in 1.5 hours.

Separately, itaconic acid and acetic anhydride in an amount of 4 times as much as said itaconic acid in view of mole were heated up to 60° to 70° C. at a reduced pressure. The reaction for anhydration was conducted while the produced acetic acid was being removed out. This method was shown in D'Alello, Gaetano F., Huemmer, T. F., Journal of Polymer Science, Polym. Chem. Ed. vol. 5, No. 2, page 307–321 (1967). The product liquid turned brown and no colorless product was obtained. This was because the reaction mixture had been exposed to 60° to 70° C. for a long time.

The use of the catalyst was found to be effective to conduct the reaction at a lower temperature for a shorter time than the comparative example and in addition prevent the product from coloring.

What is claimed is:

1. In a process for producing an organic carboxylic acid anhydride by the reaction of an organic carboxlic acid with a lower aliphatic acid anhydride, the improvement comprising conducting said reaction in the presence of from 5 to 225 parts per million, based on said organic carboxylic acid, of one or more metal ions selected from the group consisting of Co, Ni, Mn, Fe, Na, K, Mg, Ba, Ca, Cu, Zn, and Al, and at a temperature of from 20° C. up to 105° C.

2. A process as claimed in claim 1, in which said organic carboxylic acid is an aromatic carboxylic acid having at least one carboxylic group on the aromatic ring thereof.

3. A process as claimed in claim 1, in which said metal ion is an ion selected from the group consisting of Co, Ni, Mn, Fe, Na, K, Mg, Ca, Cu, Zn and Al.

4. A process as claimed in claim 1, in which said metal ion is selected from the group consisting of Co, Ni, Mn and Mg.

5. A process as claimed in claim 1, in which said organic carboxylic acid is a polycarboxylic aromatic acid having carboxylic groups on the aromatic ring in the ortho positions to each other.

6. A process as claimed in claim 1, in which said lower aliphatic acid anhydride has 1 to 5 carbon atoms.

7. A process as claimed in claim 1, in which said lower aliphatic acid anhydride is acetic anhydride or propionic anhydride.

8. A process as claimed in claim 1, in which said organic carboxylic acid is an aliphatic carboxylic acid.

9. A process as claimed in claim 3, in which said organic carboxylic acid is an aliphatic carboxylic acid.

10. A process as claimed in claim 1, in which said organic carboxylic acid is pyromellitic acid and said lower aliphatic acid anhydride is acetic anhydride.

11. A process as claimed in claim 1, in which said organic carboxylic acid is 3,4,3', 4'-benzophenonetetracarboxylic acid and said lower aliphatic acid anhydride is acetic anhydride.

12. In a process for producing an organic carboxylic anhydride which consists essentially of the reaction of an organic carboxylic acid with a lower aliphatic acid anhydride, the improvement comprising the amount of said anhydride being from 1.5 to 2.5 equivalents per equivalent of said acid and said reaction being conducted in the presence of from 5 to 225 parts per million, based on said organic carboxylic acid, of one or more Na, K, Mg, Ba, Ca, Cu, Zn and Al, and at a temperature of from 20° C. up to 105° C.

13. A process as claimed in claim 12 in which said temperature is up to 70° C.

14. A process as claimed in claim 13 in which said metal ion is cobalt ion.

15. A process as claimed in claim 12 in which said metal ions consist of nickel ions.

16. A process as claimed in claim 12 in which said metal ions consist of magnesium ions.

* * * * *

UNITED STATES PATENT AND TRADEMARK OFFICE
CERTIFICATE OF CORRECTION

PATENT NO. : 4 830 789
DATED : May 16, 1989
INVENTOR(S) : Masayoshi HINENOYA et al It is certified that error appears in the above-identified patent and that said Letters Patent is hereby corrected as shown below:

Column 10, line 29; after "more" insert ---metal ions selected from the group consisting of Co, Ni, Mn, Fe,---.

Signed and Sealed this

Twenty-third Day of January, 1990

*Attest:*

JEFFREY M. SAMUELS

*Attesting Officer*  *Acting Commissioner of Patents and Trademarks*